United States Patent [19]

Borovkov et al.

[11] Patent Number: 5,932,783
[45] Date of Patent: Aug. 3, 1999

[54] POTATO UDP-GLUCOSE PYROPHOSPHORYLASE GENE PROMOTERS AND THEIR USES

[75] Inventors: Alexander Y. Borovkov; Gary A. Secor, both of Fargo, N. Dak.

[73] Assignees: J.R. Simplot Co., Boise, Id.; North Dakota State University, Dept. of Agriculture, Bismark, N. Dak.

[21] Appl. No.: 08/630,407

[22] Filed: Apr. 1, 1996

[51] Int. Cl.[6] .............................. A01H 5/00; C07H 21/04; C12N 5/14; C12N 15/82
[52] U.S. Cl. ................. 800/298; 435/320.1; 435/419; 435/468; 536/24.1; 800/287; 800/317; 800/317.2
[58] Field of Search .............................. 435/172.3, 320.1, 435/417, 419, 468; 536/24.1; 800/205, DIG. 42, 287, 298, 317, 317.2

[56] References Cited

U.S. PATENT DOCUMENTS 5,495,071  2/1996  Fischhoff et al. ..................... 800/205

OTHER PUBLICATIONS

Katsube et al. UDP–glucose pyrophosphorylase from potato tuber: cDNA cloning an sequencing. J. Biochem. 108(2):321–326, 1990.

Spychalla et al. Cloning, antisense RNA inhibition, and the coordinated expression of UDP–glucose pyrophosphorylase with starch biosynthetic genes in potato tubers. J. Plant Physiol. 144:444–453, 1994.

*Primary Examiner*—Gary Benzion
*Assistant Examiner*—Amy J. Nelson
*Attorney, Agent, or Firm*—Townsend and Townsend and Crew, LLC

[57] ABSTRACT

The invention provides tissue specific promoters from potato UDP-glucose pyrophosphorylase (UGPase) genes. The promoters are useful in production of transgenic plants.

29 Claims, 2 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 878 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AAGCTTCACC AAATTGAAGC CCTCCTAGAC CCCAGCAAAA TCGGGTGGAG GGGCAAAACA        60
AGCCCAACAA TGCGTAAAAA TCAATCAATT GCACCATCAA TCTCATCATA ACAATCGTAA       120
CGAATTTGAA TTCATAATTT AAAATTTATG TGTTTAATTT TAAAGATTTA TAGTATCCCC       180
TCAATTTATT ATTTTTTAAA AATTTATGAT TTCAAATCTA CTATTTAACA TTATTTTAAA       240
TATTATTTCT TACATTTAGA TACACGGTGG GGCCCCCCAC TACCATGGAA ATCCAAACCA       300
AGTTTATGCC TGCGCATATT CGAACACTTT TACGTAAACA TAGAAGTTAA AAGACGAAAT       360
AATAACACTA ACGTATTTCG TGTAGTTTTT CATAAAATGA AATTTGAAAA AAATCATACA       420
CATATCTTAC CTGTATTTCA AATAGAGATA TAATTTTCAT GGACTAGTTT AAATACTTAA       480
TAAAGAATT CTTTATAGCA CGTTTGAATT ATAAAAATAA TCATTAATAT TTACGATAGA        540
GTAAAATGTT CATATTACAA AATTATTATA ATCTAATAAA AAAATATTAG GAACTCTGTC       600
GAACATGGCA TGATAGCGAA ATATTATTCT TTCCTATAAT ATTTTTCGAT ATCTCAACAA       660
TATAATTCAT AAAATCACCT TGTTAAAGA ACGGTTAGCG TTAAGTTTCA TTAGGTGTCA        720
CCTAATAGAA GAATATTTAT AGGTGTTAAC TCTTCTGGCT CTTTCCCTCT CTTCATTCAC       780
ACACTATATC TATCACTCTT CTCTCCATAC TCTCTGCTCC TCGAGAACTT TCTCTTCTCA       840
TTTCTCTCTG TAGATCACAA TCTTCTTCTC TGCCATGG                               878
```

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 9
      (D) OTHER INFORMATION: /mod_base= i (ix) FEATURE:
      (A) NAME/KEY: modified_base
      (B) LOCATION: 12
      (D) OTHER INFORMATION: /mod_base= i (ix) FEATURE:
      (A) NAME/KEY: modified_base
      (B) LOCATION: 15
      (D) OTHER INFORMATION: /mod_base= i (xi) SEQUENCE DESCRIPTION: SEQ ID NO:2:

```
TGGTATCCNC CNGGNCATGG                                                    20
```

```
(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:3:

CCAAACCANA CATCNCCNGT                                                     20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CAGTAGCCAT GGCGAAGAAG                                                     20
```

POTATO UDP-GLUCOSE PYROPHOSPHORYLASE GENE PROMOTERS AND THEIR USES

FIELD OF THE INVENTION

This invention relates generally to the use of recombinant DNA methods for genetically altering plants. In particular, it relates to new promoter sequences useful for directing expression of heterologous sequences in desired tissues.

BACKGROUND OF THE INVENTION

UTP α-D-glucose-1-phosphate uridylyl transferase, EC 2.7.7.9, (UGPase) is one of the key enzymes of carbohydrate metabolism. In photosynthetic tissue, UGPase converts glucose-1-phosphate to UDP-glucose which is a substrate for sucrose biosynthesis. Xu et al., *Plant Physiol.* 90:635–642 (1989).

UGPase activity is also associated with non-photosynthetic sink tissues such as the potato tuber. When sucrose is delivered to sink tissues, it is cleaved by sucrose synthase to UDP-glucose and fructose. UGPase then converts the UDP-glucose to glucose-1-phosphate. At this point, the hexose phosphate enters the amyloplast and serves as substrate for AGPase, and subsequently starch synthesis. Under stress conditions, starch is degraded and glucose-1-phosphate is released from the amyloplast and can then enter the same cytoplasmic sucrose biosynthetic pathway involving UGPase described above.

UGPase has been isolated and characterized from potato tubers (Nakano et al., *J Biochem.* 106: 528–532 (1989)). In addition, cDNA encoding this enzyme has been cloned and sequenced (Katsube et al., *J Biochem.* 108: 321–326 (1990)).

There is a need for a variety of different promoters to be used in the genetic engineering of plants. In particular, tissue-specific promoters which can drive expression of desired genes in particular tissues. The present invention addresses these and other needs.

SUMMARY OF THE INVENTION

The present invention provides compositions comprising an isolated nucleic acid molecule comprising a potato plant UGPase promoter. The promoters are useful for providing tissue specific expression of heterologous genes. In particular, the promoters are useful in directing expression to the roots and/or tubers of solanaceous plants.

The promoters typically comprise about 400 to about the 900 nucleotides counted upstream of the translation start site in SEQ ID No:1. In some embodiments, the promoter consists of about 600 nucleotides counted upstream of the translation start site in SEQ ID No:1.

The promoters can be included in expression cassettes for driving expression of any desired gene for which tissue specific expression is desired. Thus, the invention also provides transgenic plants comprising the expression cassettes of the invention. The plants are often members of the family Solanaceae, such as potato.

The invention also provides methods of introducing the expression cassettes of the invention into a plant. The methods can be carried out using genetic engineering techniques or by standard crosses.

Definitions

The term "UGPase gene" as used herein refers to a plant genomic DNA molecule that is the entire UGPase promoter region operably linked to the entire coding region (including exons and introns) for the UGPase protein and may include the adjacent 3' flanking region which encodes the 3' non-translated mRNA.

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes self-replicating plasmids, infectious polymers of DNA or RNA and nonfunctional DNA or RNA.

In the polynucleotide notation used herein, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "promoter" refers to a region of DNA upstream from the translational start codon and which is involved in recognition and binding of RNA polymerase and other proteins to initiate transcription. A "plant promoter" is a promoter capable of initiating transcription in plant cells.

The term "tissue-specific promoter" as used herein refers to plant promoters that are capable of selectively expressing operably linked DNA sequences, in particular plant tissues. This means that the expression of the operatively linked DNA sequences is higher in one or several plant tissues than it is in the other tissues of the plant. For example, the UGPase promoters of the invention are tissue-specific promoters that express operably linked DNA sequences in tuber or root tissue.

The term "operably linked" as used herein refers to linkage of a promoter upstream from a DNA sequence such that the promoter mediates transcription of the DNA sequence. It is understood that the promoter sequence also includes transcribed sequences between the transcriptional start and the translational start codon.

The phrase "expression cassette", refers to nucleotide sequences which are capable of effecting expression of a structural gene in hosts compatible with such sequences. Such cassettes include at least promoters and optionally, transcription termination signals. Additional factors necessary or helpful in effecting expression may also be used as described herein.

A "heterologous sequence" or a "heterologous DNA sequence", as used herein, is one that originates from a foreign source (or species) or, if from the same source, is modified from its original form. Thus, a heterologous DNA encoding sequence operably linked to a promoter is from a source different from that from which the promoter was derived, or, if from the same source, is modified from its original form. Modification of the heterologous DNA sequence may occur, e.g., by treating the DNA with a restriction enzyme to generate a DNA fragment that is capable of being operably linked to the promoter. Modification can occur by techniques such as site-directed mutagenesis.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or polypeptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein.

The term "plant" includes whole plants, plant organs (e.g., leaves, stems, roots, flowers, tubers, etc.), seeds and plant cells and progeny of same. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "transgenic plant" refers to a plant comprising heterologous nucleic acids that have been introduced into the genome by genetic engineering techniques. For example, plant cells transformed with vectors containing UGPase promoters operably linked to heterologous DNA sequences can be used to produce transgenic plants with altered phenotypic characteristics. All plants derived from the first transformed generation are also considered transgenic plants.

A "polynucleotide sequence from" a particular gene or promoter (e.g., the potato UGPase gene) is a subsequence or full length polynucleotide sequence of a gene which, when present in a transgenic plant, has the desired effect, for example, initiating expression of an operably linked gene. A full length sequence of a particular sequence or promoter disclosed here may contain about 95%, usually at least about 98% of the exemplified sequences disclosed here.

One of skill will recognize that a particular promoter sequence need not be perfectly identical and may be substantially identical to sequences specifically disclosed here to obtain the same pattern of expression. Two nucleic acid sequences are said to be "identical" if the sequence of nucleotides, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90%. and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions for a Southern hybridization using the full length promoters of the invention as probes will be those in which the salt concentration is about 0.02 molar at pH 7 and the temperature is at least about 60° C. For instance, such condition will include washing a Southern blot with 0.2X SSC at 60° C.

DESCRIPTION OF THE PREFERRED EMBODIMENT

Figure 1:
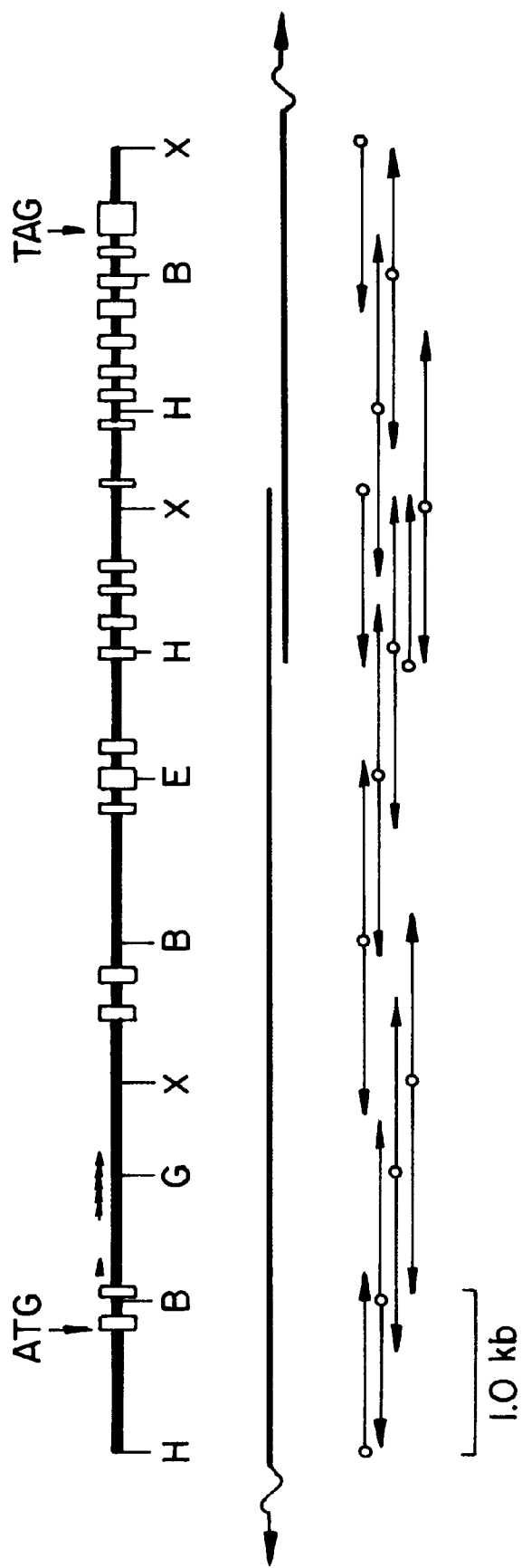
FIG. 1 shows the structure of the potato UGPase gene. Open boxes are exons. Horizontal arrows are repeats. Positions of translation start and stop sites are shown by vertical arrows. Regions of the gene contained by two overlapping λ-clones are presented by the solid bold lines below the map. The sequencing strategy is shown with arrors underneath the map. B-BamHI; G-BglII; E-EcoRI; H-HindIII; X-XbaI.

This invention provides isolated potato plant UGPase promoters and DNA constructs containing a UGPase promoter operably linked to heterologous DNA sequences. The promoters of the invention are tissue-specific and are useful in the production of transgenic plants.

A. Isolation of Plant UGPase Promoters

Plant UGPase promoter sequences are typically identical to or show substantial sequence identity (determined as described above) to the potato plant UGPase promoter nucleic acid sequence depicted in SEQ ID No:1. Plant UGPase promoter sequences typically hybridize to the nucleic acid sequence of SEQ ID No:1 under stringent conditions, as described above.

Techniques for nucleic acid manipulation of genes encoding plant UGPase such as subcloning nucleic acid sequences encoding polypeptides into expression vectors, labelling probes, DNA hybridization, and the like are described generally in Sambrook, et al., *Molecular Cloning—A Laboratory Manual* (2nd Ed.), Vol. 1–3, Cold Spring Harbor Laboratory, Cold Spring Harbor, N.Y., 1989. This manual is hereinafter referred to as "Sambrook, et al."

There are various methods of isolating genomic DNA sequences encoding plant UGPase. For example, a genomic DNA library made according to standard techniques can be probed using labelled oligonucleotide probes having sequences complementary to the promoter disclosed herein (e.g., SEQ ID No:1). Full-length promoters may be used, or oligonucleotide probes may also be generated. Such probes can be used directly in hybridization assays to isolate DNA encoding plant UGPase proteins.

Nucleic acid amplification techniques such as polymerase chain reaction (PCR) technology, can also be used to amplify nucleic acid sequences encoding UGPase proteins from genomic libraries or cDNA libraries. In PCR techniques, oligonucleotide primers complementary to the two 3' borders of the DNA region to be amplified are synthesized. The polymerase chain reaction is then carried out using the two primers. See PCR *Protocols: A Guide to Methods and Applications* (Innis, M, Gelfand, D., Sninsky, J. and White, T., eds.), Academic Press, San Diego (1990). Primers can be selected to amplify the entire regions encoding a full-length UGPase protein or its promoter. PCR can also be used to amplify smaller DNA segments of these regions as desired.

Other methods known to those of skill in the art can also be used to isolate plant DNA fragments containing UGPase promoters. See Sambrook, et al. for a description of other techniques for the isolation of DNAs related to DNA molecules of known sequence. For instance, deletion analysis and a promoterless reporter gene (e.g., GUS) can be used to identify those regions which can drive expression of a structural gene. Sequences characteristic of promoter sequences can also be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions –80 to –100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983).

Various modifications can be made to the promoters of the invention to provide promoters with different properties (e.g., tissue specificity, promoter strength, and the like). For instance, truncated forms of a UGPase promoter can be constructed by mapping restriction enzyme sites in the promoter and then using the constructed map to determine appropriate restriction enzyme cleavage to excise a subset of the sequence. The modified promoters can then be inserted into a suitable vector and tested for their ability to drive expression of a marker gene. Tissue specificity of the modified promoters can be tested in regenerated plants.

The potato UGPase promoters of the invention typically contain from 400 to 1000 nucleotides. They ate often less than about 900 nucleotides, and more usually less than about 800. A fragment of about 600 is usually sufficient to provide tissue-specific expression (in roots, tubers, and stems, but not in leaves).

B. Construction of Vectors Containing a UGPase Promoter Operably Linked to a Heterologous DNA Sequence Once a plant UGPase promoter region has been isolated, various methods may be used to construct expression cassettes, vectors and other DNA constructs. A variety of techniques can be used for these manipulations of nucleic acids. These techniques are known to those of skill in the art and are described generally in Sambrook, et al., supra.

Expression cassettes containing a UGPase promoter can be constructed in a variety of ways. For instance, various procedures, such as site directed mutagenesis can be used to introduce a restriction site at the start codon of a UGPase gene fragment. Then heterologous DNA sequences can be linked to the UGPase promoter such that the expression of the heterologous sequences is regulated by the promoter. DNA constructs composed of a UGPase promoter operably linked to heterologous DNA sequences can then be inserted into a variety of vectors. Such vectors include expression vectors that are useful in the transformation of plant cells. A variety of vectors useful in the transformation of plant cells can be constructed by the use of recombinant DNA techniques well known to those of skill in the art.

C. Production of Transgenic Plants

DNA constructs containing a UGPase promoter operably linked to a heterologous DNA sequence can be used to transform plant cells and produce transgenic plants with desired phenotypic characteristics. There are a variety of different approaches one can use to produce a desired phenotype in transgenic plants. For example, by using methods described herein, one can operably link a heterologous gene to a UGPase promoter and transform plant cells. Transgenic plants can be produced from the transformed plant cells so that the heterologous gene product is produced in certain tissues (e.g., the tuber) of a transgenic plant. In this context, the term "heterologous gene" refers to a gene that is not normally present in a plant or which, if present, is not normally expressed in a particular plant cell tissue. The expression of the gene can result in the production of a protein that confers an altered phenotype on a transgenic plant.

A variety of genes capable of altering a plant phenotype can be expressed with a UGPase promoter. Suitable genes include the following: UGPase, invertase, and polyphenyl oxidase, all of which are typically in the antisense orientation. One of skill will recognize that proteins have different domains which perform different functions. Thus, gene sequences operably linked to a UGPase promoter need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

DNA constructs containing a UGPase promoter operably linked to a heterologous DNA sequence can also be used in a number of techniques to suppress expression of endogenous plant genes. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous ovule-specific gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of ovule-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585–591 (1988).

Another method of suppression is sense suppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Asparagus, Atropa, Avena, Beta, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Sacchromyces, Secale, Senecio, Sinapis, Solanum, Sorghum, Trigonella, Triticum, Vitis, Vigna, and, Zea. Typically, plants used in the invention will be those in which starch and/or sugar synthesis or of economic importance. Such crops include, potatoes, corn, sugar beet, and sugar cane.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The following examples are provided by way of illustration and not limitation.

MATERIALS AND METHODS

General Techniques

All regular molecular biology procedures were carried out as described by Sambrook et al. (supra). Alkaline capillary transfer was used to transfer DNA from agarose gel to Hybond-$N^+$ membrane. $^{32}$P-labeled probe was prepared using a Random Primer DNA Labeling Kit (BRL). Double-stranded plasmid DNA was sequenced using Sequenase Version 2.0 Sequencing Kit (United States Biochemical). UGPase activity was measured as described by Sowolinos Plant Physiol 57:63–68 (1976).

PCR Amplification of a Fragment of Potato UGPase Gene

Total DNA was extracted from greenhouse grown potato plants (*Solanum tuberosum* L. cv. Red Pontiac) by the procedure described by Shure et al., *Cell* 35: 225–233 (1983). A fragment of the UGPase gene was amplified from potato genomic DNA by a set of the specific primers (5'-TGGTATCCICCIGGICATGG-3' (SEQ ID No:2) and 5'-CCAAACCAIACATCICCIGT-3'(SEQ ID No:3)) based on the amino acid sequence published by Nakano et al., *J Biochem* 106: 528–532 (1989) and contained deoxyinosine impositions of redundant nucleotides. 500 μg of potato DNA was amplified in 100 μl of IX Taq DNA polymerase buffer (Promega Corporation) supplemented with 1 μM of each primer, 200 μM of each deoxynucleotide, and 5 units of Taq DNA polymerase. Amplification was performed for 35 cycles consisting of 1 min at 94° C., 1 min at 55° C., and 1.5 min at 72° C. During the last cycle, the polymerization step was extended to 7 min.

Genomic Library Screening

Lambda FIX II library (Stratagene) of potato (*Solanum tuberosum* L. cv Lemhi) genomic DNA obtained from after one round of amplification was partially digested with Sau3 A and used for isolation of the UGPase gene. Approximately 2×10$^6$ lambda clones were plated on each of six plates (180 mm) with an *E. coli* lawn. Two replicas of each plate were made on Hybond-$N^+$ nylon membrane. After hybridization with the $^{32}$P-labeled PCR generated fragment of the UGPase gene, the agar plugs were taken from the areas corresponding to the positive signals on both replicas. Phage particles were eluted from the plugs and replated at a concentration of approximately 100 pfu per plate. After rescreening these plates with the same probe, single positive plaques were selected and used for further analysis.

Primer Extension

Total RNA was isolated from potato leaves and tubers (cv. Russet Burbank) as described by Logemann et al., *Anal Biochem* 163: 16–20 (1987). The primer extension reaction was carried out as described by Belanger and Kxiz *Genetics* 129: 863–872 (1991), except total RNA was used instead of poly(A)-RNA. A 20-mer primer 5'-CAGTA-GCCATGGCGAAGAAG-3' (SEQ ID No:4) (5-UP) complementary to the translation start region of the UGPase mRNA and containing NcoI restriction site in position of ATG start codon was used to prime the reaction. To identify the 3'-end of the synthesized cDNA, the products were separated on denaturing 5% polyacrylamide gel side-by-side with sequencing reactions of the corresponding region of the gene, primed with 5-LTP. A RNAse treated RNA sample was used as a negative control.

Amplification of 5'-cDNA Ends (5'-RACE)

5'-RACE of potato UGPase mRNA was carried out using Marathon cDNA Amplification Kit (Clontech) as described in the product protocol. Total RNA from potato leaves, stems, developing and stored tubers (cv. Russet Burbank) was used for cDNA synthesis. 5-UP primer was used for specific amplification of 5'-region of UGPase cDNA.

Cloning of Potato UGPase Promoter Region

Figure 2:
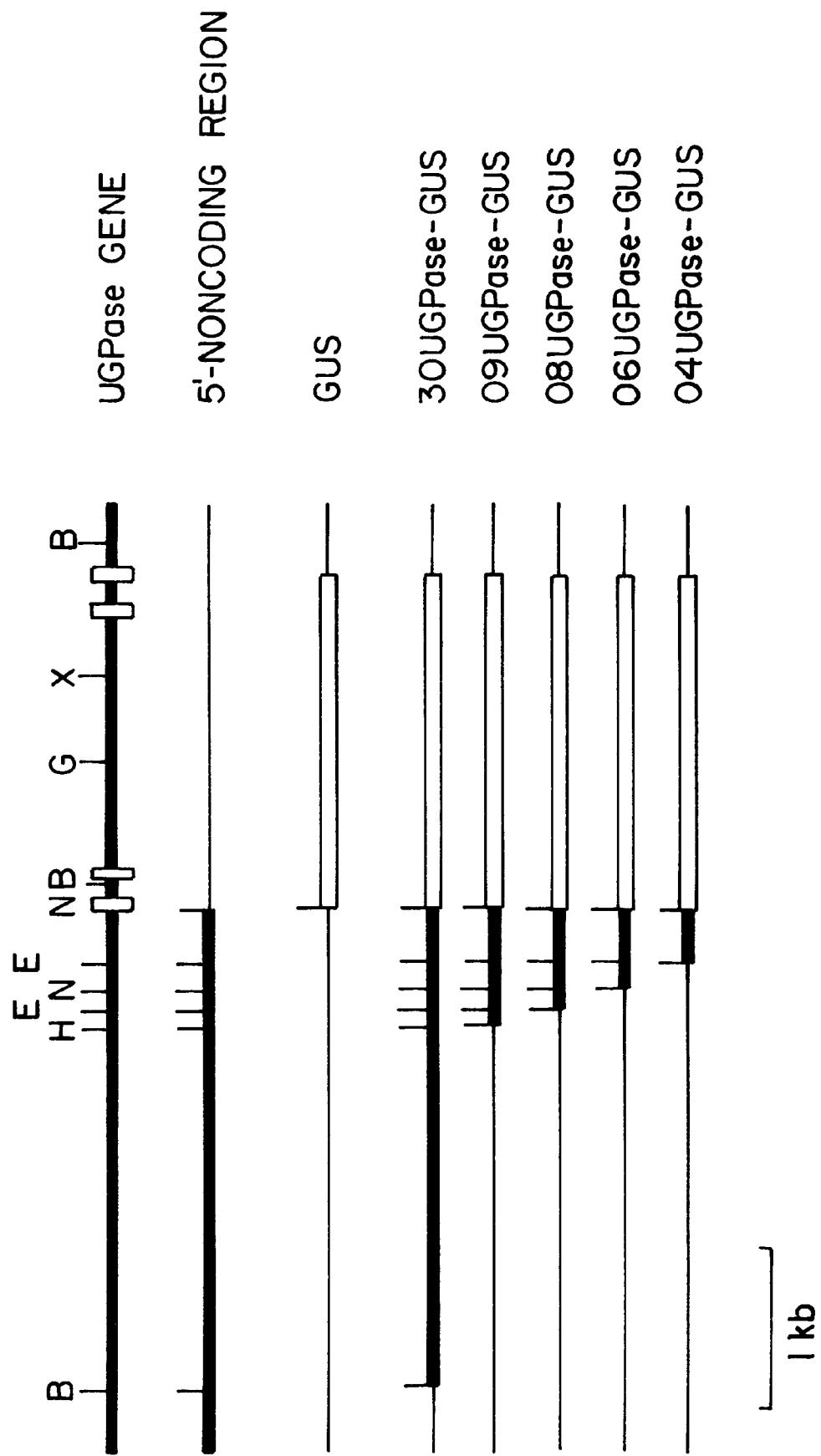
FIG. 2 shows construction of the artificial UGPase-GUS gene and the stepwise deletions of the UGPase promoter region. The constructs contain 388 bp, 590 bp, 745 bp, 874 bp and 3 kb fragments of the potato gene respectively.

The 7 kb XbaI fragment of potato UGPase gene containing a part of the coding region and a 5.5 kb region upstream from the translation start codon was used for the promoter analysis. A NcoI restriction site in position of the ATG codon was PCR generated using the 5-UP primer. This site was used to fuse the upstream regions of UGPase gene, with the modified β-glucuronidase (GUS) coding sequences, that also contained NcoI site in the position of the translation start codon. Using convenient EcoRI, HindIII, NcoI sites five stepwise deletions of the promoter were generated and cloned in pBluescript SK$^+$ (Stratagene) (FIG. 2).

Transient GUS Expression

A particle-inflow gun was used for particle bombardment of tobacco leaves. The coating of tungsten particles with CsCl gradient purified plasmid DNA, and the bombardment was carried out exactly as described by Finer et al. *Plant Cell Rep* 11: 323–328 (1992).

After bombardment leaves, were placed on MS medium and incubated overnight at room temperature. The next day leaves were vacuum impregnated with a staining solution containing 1 mmol/L X-Glucuronide, 0.5 mmol/L $K_3Fe(CN)_6$, 10 mmol/L $Na_2$-EDTA, 0.1% Triton X-100, 0.1 mol/L sodium phosphate buffer, pH 7.0. After impregnation, leaves were incubated in the staining solution 24 hours at 37° C. and then bleached by boiling in several changes of 50% ethanol.

Transformation of Potato

The chimeric UGPase-GUS constructs described above and shown in FIG. 2 were subcloned into binary vector pBIN19 (Bevan, *Nucl Acids Res* 12:8711–8721 (1984)) and used for transformation potato (*Solanum tuberosum* L. cv. Russet Burbank) and tobacco (*Nicotiana tabacum*) plants as described previously (Snyder et al., *Plant Cell Rep* 12: 324–327 (1993)). Kanamycin resistant plants were selected and presence of the chimeric gene was confirmed by PCR. The greenhouse grown plants were used for GUS assay using the procedure described above.

RESULTS AND DISCUSSION

Structure of The Potato UGPase Gene

Two overlapping λ-clones were isolated from a potato genomic DNA library. 0.5–3.0 kb fragments of the inserts were subcloned in pGEM4Z (Promega) and sequenced. The physical map, intron/exon structure of the gene, and the sequencing strategy are shown on FIG. 1. Neither λ-clone contained the entire gene. One clone contained approximately three quarters of the coding region and 5.5 kb of the 5' adjoining sequence. The other contained the last third of the gene and approximately 8 kb of the 3' adjoining sequence. Because the potato genome contains a single UGPase gene, the sequences of these two clones were combined to reconstruct the entire structure of the gene. The full length sequence of the gene is deposited at the EMBL databank as accession number U20345.

The region between the translation start and stop sites is 6600 nt long. It contains 20 exons, ranging from 24 to 124 nt, and 19 introns, ranging from 77 to 1598 nt. The sequence downstream from the translation stop site was identical to the published 3'-noncoding sequences of the UGPase mRNA (Katsube et al., *J Biochem* 108:321–326 (1990) and Spychalla et al., *J. Plant Physiol.* 144:444–453 (1994)). A putative polyadenylation site was found 79 bp downstream of the translation stop codon.

Although at least two different UGPase alleles were found in most potato cultivars, a comparison of the UGPase sequence from cv. Lemhi, presented here, and the sequence of the PCR-generated fragment of the UGPase gene from cv. Red Pontiac (data not shown) did not reveal a single nucleotide difference. The coding region was highly homologous with two cloned UGPase cDNAs. It differed from the UGPase cDNA from cv. Danshaku-Imo at three bases (see, Katsube et al., supra). One difference resulted in a change of the proline at position 66 to leucine. The UGPase cDNA from cv. Desiree differed from the coding region at 25 bases and five of these caused the change of Thr, Tyr, Lys, Lys and Val at positions 5, 30, 82, 445 and 450 to Ala, Asp, Asn, Glu and Ile, respectively (see, Spychalla et al., supra).

The largest intron (number 2) contains six copies of a highly conserved direct repeat. One copy was isolated from the other five, which formed a direct tandem repeat (FIG. 1). The repeat consists of a 50-nt core unit flanked by GT regions of different lengths. No specific signals were found in the region using the Signal Scan ver. 3.3 computer program [11]. The BLAST (Basic Local Alignment Search Tool) search of Genbank and EMBL databases did not reveal significant homology between the repeat and any known sequence. The role of the repeat is unknown, but computer analysis (PCFOLD ver. 4.0 [22]) of the secondary structure of the transcribed RNA showed that it can form a number of hairpins.

Localization of Transcriptional Start Sites

Primer extension of UGPase mRNA from potato tubers revealed several products. The cDNA synthesis was terminated 84, 124, 322 and 422 nt upstream from the translation start. The absence of these cDNA products in a RNAse-treated control indicates that the extension products were synthesized on a RNA and not a DNA matrix.

Southern hybridization of the direct products of 5'-RACE of UGPase mRNA from potato tubers with a $^{32}$P-labeled fragment of the gene, showed the presence of two major products of about 120 and 80 bp and a minor product of 320 bp. The same pattern, but with much lower intensity of the 120 and 80 bp fragments was detected in products of RNA from stem tissue. Only the 320 bp fragment, with approximately the same intensity as the tuber and stem products, was detected in leaf RNA. Attempts to clone these fragments were successful only for the 80 bp fragment. The actual size of the cloned fragment was 83 bp.

The potato UGPase cDNAs from cv. Desiree has a 83 nt long 5'-noncoding region, which is one nucleotide shorter than the shortest fragment generated by the primer extension and matches the genomic sequence and the sequence of the cloned 5'-RACE product. The 5'-noncoding region UGPase cDNA from cv. Danshaku-Imo is 123 nt long and may correspond to the 120 bp the 5'-RACE product. With the exception of first 24 nucleotides, the region is also homologous to the genomic DNA. Although a sequence homologous to this 24 nt sequence was not found within a 5.5 kb region of genomic DNA upstream from the translation start site, the complimentary sequences was found in 3'-noncoding region of both the gene and cDNA.

The presence of a seven-nucleotide-long inverted repeat in the potato UGPase gene may cause artificial modification of the 5'-end of the UGPase cDNA during cloning. If prior to the second strand synthesis, the cDNA forms a loop by annealing units of the inverted repeat, its free 3'-end could be degraded to the duplex by the 3'→5' exonuclease activity of DNA polymerase. The enzyme could then extend the 3'-end, using the 5'-end of the cDNA as a template. As a result, the seven-nucleotide-long repeat at the 5'-end of the cDNA will be extended into a sequence complimentary to the 3'-end of the molecule. This model can explain the formation of the inverted repeat in cDNA described by Katsube et al., but the region matching the genomic sequence in this cDNA is also 18 nucleotides longer than in the cDNA described by Spychalla et al. This fact can be explained only if the mRNA, used for the cDNA synthesis, was initiated further than 84 nt upstream from translation start site.

The difference between these two cDNAs may represent allelic difference between the genotypes. Most potato cultivars including Desiree, used by Spychalla et al., and Russet Burbank, used here, contain at least two different allelic forms of UGPase mRNA. Two independent groups working with cv. Desiree noted two UGPase mRNAs after northern hybridization. We also saw a similar northern hybridization pattern from cv. Russet Burbank (not presented). Further, the results of the primer extension and the 5'-RACE presented here also indicate presence of multiple UGPase mRNAs with different 5'-noncoding region lengths. Additional analysis is needed to confirm their nature of these mRNAs.

Analysis of the UGPase Promoter

Five different UGPase-GUS constructs were used to investigate the organization of the UGPase gene promoter. Each was tested for its ability to drive GUS expression in the particle bombarded and Agrobacterium-transformed plant tissues. Transient GUS expression was detected in tobacco and bean leaves bombarded with all but one construct (FIG. 2). The relative numbers of blue spots detected on the leaves after bombardment were counted to compare efficiency of different constructs. The results are summarized in Table 1. No foci were found on the leaves bombarded with 04UGPase-GUS. From several hundred to over one thousand foci were detected on the leaves bombarded with the four other constructs. The number of foci increased up to 874 bp, and the leaves bombarded with 09UGPase-GUS showed highest level of GUS expression. The further extension of the promoter length resulted in more than 50% drop in activity.

Transgenic potato plants transformed with all but the 04UGPase-GUS construct expressed GUS in most tissues. The highest level of the enzyme activity was detected in 09UGPase-GUS transformed plants. The length of the promoter did not affect the tissue specificity of the gene expression. The highest level of GUS activity was detected in stems. The activity in roots and stolons was greater than in petioles and tubers, and no detectable activity was noted in leaves. The level of GUS activity generally correlated with the level of UGPase activity detected in same tissue of non-transgenic potato plants, which were: leaf 224±17.8, stem 1257.7±162.2, root 957.3±85.2 and tuber 881.5±89.7 units/mg total protein.

An analysis of transgenic tobacco plants demonstrated that all except the 04UGPase-GUS transformed plants expressed GUS in stems and petioles, lower in leaves, and none in roots. The highest level was detected in tobacco plants transformed with 09UGPase-GUS.

On the basis of results of the performed analysis we can draw a sketch of the promoter structure. First, the 590 bp fragment carried by 06UGPase-GUS construction contains all elements of the promoter essential for normal UGPase expression, including those responsible for tissue-specificity of the gene expression, while the 388 bp fragment carried by 04UGPase-GUS construct is not sufficient to express the gene. Analysis of primary structure of the UGPase promoter region revealed several TATA-box motifs, located 214, 239, 365 and 426 nt upstream from the translation start, and only one CAAT-box motif, located 454 nt upstream from the translation start. The 426 nt TATAbox and the CAAT-box motifs were missing in the 04UGPase-GUS construct.

Secondly, the difference in tissue specificity of the expression of the same chimeric gene in tobacco and potato plants indicates the presence of cis-acting elements that are regulated by trans-acting factors specific to potato. These elements should be located in the 590 bp fragment of the promoter, carried by 06UGPase-GUS construct, and should enhance activity of the promoter in roots and suppress it in leaves.

Third, the increase of the GUS activity relative to the length of the construct indicates the presence of additional regulatory elements. Those elements that enhance expression of the promoter should be located in the 874 bp region and those which suppress activity would be further upstream.

TABLE 1

| Transient GUS expression in the particle bombarded tobacco leaves | |
|---|---|
| Construct | Relative number of blue foci (%)[1] |
| GUS w/out promoter | 0 |
| 04UGPase-GUS | 0 |
| 06UGPase-GUS | 100[2] |
| 08UGPase-GUS | 146 ± 7 |
| 09UGPase-GUS | 282 ± 4 |
| 30UGPase-GUS | 138 ± 6 |

[1]Based on results of five independent experiments.
[2]The number of loci at the leaves bombarded with 06UGPase-GUS was counted as 100%.

The above examples are provided to illustrate the invention but not to limit its scope. Other variants of the invention will be readily apparent to one of ordinary skilled in the art and are encompassed by the appended claims. All publications, patents, and patent applications cited herein are hereby incorporated by reference for all purposes.

```
            HindIII                                                             SEQ ID NO:1.
      1 aagcttcacc aaattgaagc cctcctagac cccagcaaaa tcgggtggag gggcaaaaca 61 agcccaacaa tgcgtaaaaa tcaatcaatt gcaccatcaa tctcatcata acaatcgtaa EcoRI
    121 cgaatttgaa ttcataattt aaaatttatg tgtttaattt taaagattta tagtatcccc 181 tcaatttatt attttttaaa aatttatgat ttcaaaccta ctatttaaca ttattttaaa
                                                              NcoI
    241 tattatttct tacatttaga tacacggtgg ggccccccac taccatggaa atccaaacca 301 agtttatgcc tgcgcatatt cgaacacttt tacgtaaaca tagaagttaa aagacgaaat 361 aataacacta acgtatttcg tgtagttttt cataaaatga aatttgaaaa aaatcataca 421 catatcttac ctgtatttca aatagagata taattttcat ggactagttt aaatacttaa EcoRI
    481 taaaagaatt ctttatagca cgtttgaatt ataaaaataa tcattaatat ttacgataga 541 gtaaaatgtt catattacaa aattattata atctaataaa aaaatattag gaactctgtc 601 gaacatggca tgatagcgaa atattattct ttcctataat atttttcgat atctcaacaa 661 tataattcat aaaatcacct ttgttaaaga acggttagcg ttaagtttca ttaggtgtca TATA-box
    721 cctaatagaa gaatatttat aggtgttaac tcttctggct ctttccctct cttcattcac

| start transcription
    781 acactatatc tatcactctt ctctccatac tctctgctcc tcgagaactt tctcttctca NcoI
    841 tttctctctg tagatcacaa tcttcttctc tgccATGG
                                             | start translation
```

What is claimed is:

1. A composition comprising an isolated or recombinant nucleic acid molecule comprising a potato plant UGPase promoter, wherein the UGPase promoter consists of about 400 to about 900 nucleotides upstream of the translation start codon in SEQ ID NO:1.

2. A composition comprising an isolated or recombinant nucleic acid molecule comprising a potato plant UGPase promoter, wherein the UGPase promoter consists of about 600 nucleotides upstream of the translation start codon in SEQ ID NO:1.

3. An isolated or recombinant nucleic acid molecule comprising a promoter sequence which initiates transcription in plant cells, wherein the nucleic acid molecule hybridizes to SEQ ID NO:1 under stringent hybridization conditions.

4. The isolated or recombinant nucleic acid molecule of claim 3, wherein the stringent hybridization conditions comprise hybridization in a salt concentration of about 0.02 molar at pH 7 and a temperature of about 60° C.

5. The isolated or recombinant nucleic acid molecule of claim 3, wherein the stringent hybridization conditions comprise washing at 65° C. in 0.1X SSC,0.1% SDS.

6. The isolated or recombinant nucleic acid molecule of claim 3, which is about 400 to about 900 nucleotides upstream of the translation start codon in SEQ ID NO:1.

7. The isolated or recombinant nucleic acid molecule of claim 3, which is about 600 nucleotides upstream of the translation start codon in SEQ ID NO:1.

8. The isolated or recombinant nucleic acid molecule of claim 3, wherein the promoter sequence initiates transcription in plant cells in a tissue specific manner.

9. The isolated or recombinant nucleic acid molecule of claim 7, wherein the promoter sequence provides tissue-specific expression in roots, tubers and stems.

10. A recombinant expression cassette comprising a potato plant UGPase promoter operably linked to a heterologous nucleic acid sequence, wherein the promoter consists of about 400 to about 900 nucleotides upstream of the translation start codon in SEQ ID NO:1.

11. A recombinant expression cassette comprising a potato plant UGPase promoter operably linked to a heterologous nucleic acid sequence, wherein the promoter consists of about 600 nucleotides upstream of the translation start codon in SEQ ID NO.1.

12. A recombinant expression cassette comprising a nucleic acid sequence which initiates transcription in plant cells, wherein the nucleic acid sequence hybridizes to SEQ ID NO:1 under stringent hybridization conditions.

13. A vector comprising a potato plant UGPase promoter operably linked to a heterologous nucleic acid sequence, wherein the UGPase promoter consists of about 400 to about 900 nucleotides upstream of the translation start codon in SEQ ID NO:1.

14. A vector comprising a potato plant UGPase promoter operably linked to a heterologous nucleic acid sequence, wherein the UGPase promoter consists of about 600 nucleotides upstream of the translation start codon in SEQ ID NO:1.

15. A vector comprising a nucleic acid sequence which initiates transcription in plant cells, wherein the nucleic acid sequence hybridizes to SEQ ID NO:1 under stringent hybridization conditions.

16. A transgenic plant comprising a nucleic acid sequence which initiates transcription in plant cells, wherein the nucleic acid sequence hybridizes to SEQ ID NO:1 under stringent hybridization conditions.

17. The transgenic plant of claim 16, wherein the stringent hybridization conditions comprise hybridization in a salt concentration of about 0.02 molar at pH 7 and a temperature of about 60° C.

18. The transgenic plant of claim 16, wherein the nucleic acid molecule comprises a plant promoter operably linked to a heterologous nucleic acid sequence.

19. The transgenic plant of claim 16, wherein the plant promoter consists of about 400 to about 900 nucleotides upstream of the translation start codon in SEQ ID NO:1.

20. The transgenic plant of claim 16, wherein the plant promoter consists of about 600 nucleotides upstream of the translation start codon in SEQ ID NO:1.

21. The transgenic plant of claim 16, wherein the plant is a member of the family Solanaceae.

22. The transgenic plant of claim 21, wherein the plant is a potato plant.

23. The transgenic plant of claim 18, wherein the plant promoter initiates transcription of the heterologous nucleic acid sequence in a tissue specific manner.

24. The transgenic plant of claim 23, wherein the plant promoter provides tissue-specific expression of the heterologous nucleic acid sequence in roots, tubers and stems.

25. The transgenic plant of claim 18, wherein the heterologous nucleic acid sequence is expressed in an antisense orientation.

26. The transgenic plant of claim 25, wherein the heterologous nucleic acid sequence is selected from the group consisting of UGPase, invertase, and polyphenyl oxidase.

27. A method of expressing a heterologous nucleic acid sequence in a plant cell comprising:

a) transforming said plant cell with a vector or an expression cassette comprising a potato plant UGPase promoter, wherein the UGPase promoter consists of about 400 to about 900 nucleotides upstream of the translation start codon in SEQ ID NO:1, and wherein the promoter is operably linked to the heterologous nucleic acid sequence; and wherein the heterologous nucleic acid sequence is expressed in said plant cell.

28. A method of expressing a heterologous nucleic acid sequence in a plant cell comprising:

a) transforming said plant cell with a vector or an expression cassette comprising a potato plant UGPase promoter, wherein the UGPase promoter consists of about 600 nucleotides upstream of the translation start codon in SEQ ID NO:1, and wherein the promoter is operably linked to the heterologous nucleic acid sequence; and wherein the heterologous nucleic acid sequence is expressed in said plant cell.

29. A method of expressing a heterologous nucleic acid sequence in a plant cell comprising:

a) transforming said plant cell with a vector or an expression cassette comprising a promoter that initiates transcription in plant cells, wherein the promoter comprises a nucleic acid sequence which hybridizes to SEQ ID NO:1 under stringent hybridization conditions, and wherein the promoter is operably linked to the heterologous nucleic acid sequence; and wherein the heterologous nucleic acid sequence is expressed in said plant cell.

* * * * *